United States Patent
Martin et al.

(10) Patent No.: US 11,896,581 B2
(45) Date of Patent: Feb. 13, 2024

(54) COMPOSITIONS AND METHODS FOR PROVIDING HEALTH BENEFITS IN AN ANIMAL

(71) Applicant: Société des Produits Nestlé S.A., Vevey (CH)

(72) Inventors: Francois-Pierre Martin, Vuisternens-Devant-Romont (CH); Christian Darimont-Nicolau, Lausanne (CH); Andreas Rytz, Carrouge (CH)

(73) Assignee: SOCIÉTÉ DES PRODUITS NESTLÉ S.A., Vevey (CH)

( * ) Notice: Subject to any disclaimer, the term of this patent is extended or adjusted under 35 U.S.C. 154(b) by 246 days.

(21) Appl. No.: 17/398,499

(22) Filed: Aug. 10, 2021

(65) Prior Publication Data

US 2022/0071962 A1   Mar. 10, 2022

Related U.S. Application Data

(60) Provisional application No. 63/074,723, filed on Sep. 4, 2020.

(51) Int. Cl.
| | |
|---|---|
| A61K 31/4172 | (2006.01) |
| A23K 20/142 | (2016.01) |
| A23K 50/40 | (2016.01) |
| A23K 20/121 | (2016.01) |
| A61K 31/192 | (2006.01) |
| A61K 45/06 | (2006.01) |

(52) U.S. Cl.
CPC ........ *A61K 31/4172* (2013.01); *A23K 20/121* (2016.05); *A23K 20/142* (2016.05); *A23K 50/40* (2016.05); *A61K 31/192* (2013.01); *A61K 45/06* (2013.01)

(58) Field of Classification Search
CPC .... G06F 3/0652; G06F 3/0619; G06F 3/0653; G06F 3/0683; G06F 11/004
See application file for complete search history.

(56) References Cited

U.S. PATENT DOCUMENTS

| | | | |
|---|---|---|---|
| 5,763,392 | A | 6/1998 | Hansen et al. |
| 5,834,032 | A | 11/1998 | Song |
| 5,952,033 | A | 9/1999 | Anantharaman et al. |
| 5,968,569 | A | 10/1999 | Cavadini et al. |
| 6,203,825 | B1 | 3/2001 | Hodgkins |
| 6,929,793 | B2 | 8/2005 | Spivey-Krobath et al. |
| 7,189,390 | B2 | 3/2007 | Zink et al. |

(Continued)

FOREIGN PATENT DOCUMENTS

| | | |
|---|---|---|
| CN | 1452971 | 11/2003 |
| CN | 1504190 | 6/2004 |

(Continued)

OTHER PUBLICATIONS

English Translation of CN 103355548 (Year: 2013).*

(Continued)

*Primary Examiner* — Savitha M Rao
*Assistant Examiner* — Andrew P Lee

(57) ABSTRACT

The present disclosure provides compositions and methods for providing a health benefit to an animal utilizing ferulic acid and histidine. For example, a composition can contain ferulic acid and histidine in therapeutically effective amounts for providing the health benefit to the animal.

20 Claims, 2 Drawing Sheets

(56) References Cited

U.S. PATENT DOCUMENTS

| | | | |
|---|---|---|---|
| 9,861,116 B2 | 1/2018 | Al-Murrani | |
| 2010/0204204 A1* | 8/2010 | Zaworotko | A61K 31/522 514/474 |
| 2013/0017283 A1 | 1/2013 | Zemel et al. | |
| 2018/0021391 A1 | 1/2018 | Burcelin et al. | |

FOREIGN PATENT DOCUMENTS

| | | |
|---|---|---|
| CN | 1506048 | 6/2004 |
| CN | 103355548 A | 10/2013 |
| CN | 109331113 A | 2/2019 |
| EP | 1143806 B1 | 4/2006 |
| EP | 1641352 | 4/2006 |
| EP | 1296565 B1 | 8/2006 |
| EP | 1482811 B1 | 8/2006 |
| EP | 1213970 B1 | 6/2008 |
| EP | 2315532 B1 | 8/2014 |
| EP | 1835817 B1 | 2/2018 |
| WO | 2013076121 | 5/2013 |
| WO | 2016020486 | 2/2016 |
| WO | 2016020495 | 2/2016 |

OTHER PUBLICATIONS

Okamoto et al, Archives of Biochemistry and Biophysics, vol. 491, Issues 1-2, Nov. 2009, pp. 46-52.

Tallarida, R.J., Quantitative methods for assessing drug synergism. Genes Cancer 2, Dec. 2011, pp. 1003-1008.

Tallarida, R.J. Revisiting the isobole and related quantitative methods for assessing drug synergism. J Pharmacol Exp Ther vol. 342, Feb. 2012, pp. 2-8.

International Search Report and Written Opinion to PCT/IB2021/057384 dated Oct. 28, 2021.

Panwar Richa et al "In-vivo sustained release of nanoencapsulated ferulic acid and its impact in induced diabetes" Materials Science and Engineering, Jun. 2018 pp. 381-392 XP085462447.

* cited by examiner

COMPOSITIONS AND METHODS FOR PROVIDING HEALTH BENEFITS IN AN ANIMAL

CROSS REFERENCE TO RELATED APPLICATION

This application claims priority to U.S. Provisional Application Ser. No. 63/074,723 filed Sep. 4, 2020 the disclosure of which is incorporated in its entirety herein by this reference.

BACKGROUND

Diabetes (diabetes mellitus) is a common lifestyle-related disease. A symptom of the diabetes is characterized by continuous high concentration of blood glucose. Additionally, diabetes causes various other diseases/complications such as diabetic neuropathy, diabetic hypertonia and diabetic arteriosclerosis, in addition to diabetic blindness and urinemia.

Diabetes can be classified into two types. One is Type 1 diabetes, also called an insulin-dependent diabetes. Type 1 diabetes refers to those subjects that are not able to secrete insulin. Type II diabetes refers to those subjects where secreted insulin is impaired. Notably, those having Type II diabetes may additionally have other health challenges such as obesity, mental stresses, or lack of physical activity.

Diabetes can be found across species. For example, an American study has reported the prevalence increasing over the past 30 years, from 1 in 1250 (0.08%) in 1970 to 1 in 81 (1.2%) in 1999, though the contribution of increased diagnosis versus increased prevalence is unclear. In England, diabetes in cats is considered as a relatively common disease and is associated with high mortality. Hence, type 2 diabetes not only represents a health problem for this population but also a burden for the pet owner since they must ensure daily insulin injections for their diabetic cats.

There is, therefore, a need for methods and compositions to address diabetes and associated conditions for better health and wellness of animals.

SUMMARY

In one embodiment, a composition for providing a health benefit to an animal can comprise ferulic acid and histidine, where the composition contains ferulic acid and histidine in therapeutically effective amounts for providing the health benefit to the animal.

In another embodiment, a method for providing a health benefit to an animal can comprise administering a composition to the animal, wherein the composition comprises ferulic acid and histidine in therapeutically effective amounts for providing the health benefit to the animal.

Other and further objects, features, and advantages of the invention will be readily apparent to those skilled in the art.

DETAILED DESCRIPTION

Definitions

Figure 1:
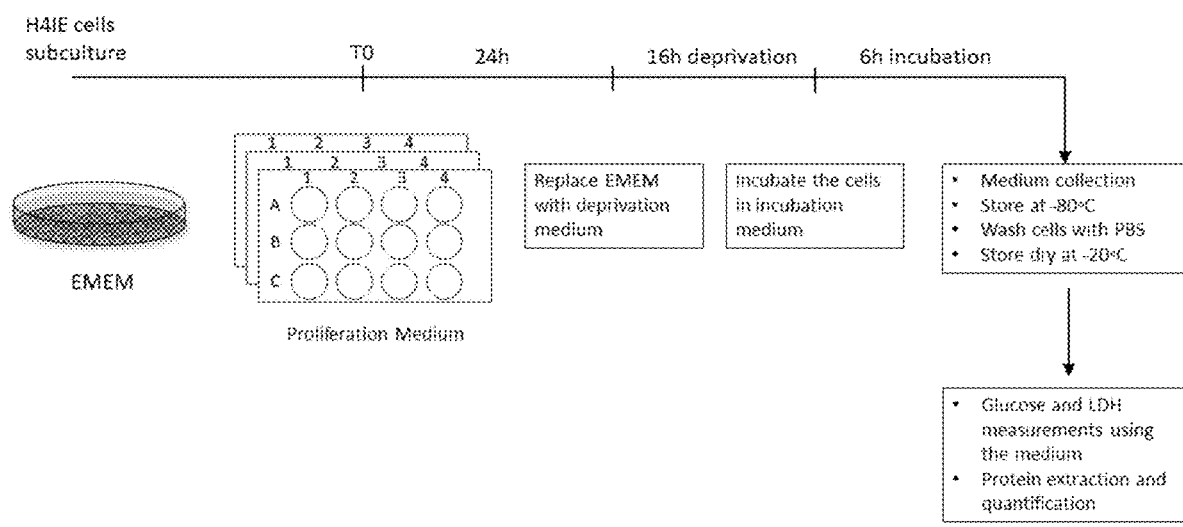
FIG. 1 is a schematic diagram of the experimental design in accordance with Example 1.

The term "animal" means any animal that has a need for preserving lean body mass during weight loss, including human, avian, bovine, canine, equine, feline, hircine, lupine, murine, ovine, or porcine animals. In one aspect, the animal can be a mammal.

The term "companion animal" means domesticated animals such as cats, dogs, rabbits, guinea pigs, ferrets, hamsters, mice, gerbils, horses, cows, goats, sheep, donkeys, pigs, and the like. In one aspect, the companion animal can be a canine. In another aspect, the companion animal can be a canine and/or a feline.

The term "therapeutically effective amount" means an amount of a compound disclosed herein that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "treating", "treat", and "treatment" embrace both preventative, i.e., prophylactic, and palliative treatment.

The term "health and/or wellness of an animal" means the complete physical, mental, and social well-being of the animal, not merely the absence of disease or infirmity.

The term "in conjunction" means that the food composition, components thereof, or other compositions disclosed herein are administered to an animal (1) together in a single food composition or (2) separately at the same or different frequency using the same or different administration routes at about the same time or periodically. "Periodically" means that the food composition, components thereof, or other compositions are administered on a schedule acceptable for specific compounds or compositions. "About the same time" generally means that the food composition, components thereof, or other compositions are administered at the same time or within about 72 hours of each other.

The term "food" or "food product" or "food composition" means a product or composition that is intended for ingestion by an animal, including a human, and provides nutrition to the animal.

The term "carbohydrate" refers to carbohydrates that are digestible, e.g. sugars and starches, and does not include fiber, e.g. cellulose or fermentable fibers.

The term "regular basis" means at least monthly administration and, in one aspect, at least weekly administration. More frequent administration or consumption, such as twice or three times weekly, can be performed in certain embodiments. In one aspect, an administration regimen can comprise at least once daily consumption.

The term "single package" means that the components of a kit are physically associated in or with one or more containers and considered a unit for manufacture, distribution, sale, or use. Containers include, but are not limited to, bags, boxes, cartons, bottles, packages such as shrink wrap packages, stapled or otherwise affixed components, or combinations thereof. A single package may be containers of the food compositions, or components thereof, physically associated such that they are considered a unit for manufacture, distribution, sale, or use.

The term "virtual package" means that the components of a kit are associated by directions on one or more physical or virtual kit components instructing the user how to obtain the other components, e.g., in a bag or other container containing one component and directions instructing the user to go to a website, contact a recorded message or a fax-back service, view a visual message, or contact a caregiver or instructor to obtain instructions on how to use the kit or safety or technical information about one or more components of a kit.

The term "about" means plus or minus 20% of a numeric value; in one aspect, plus or minus 10%; in another aspect, plus or minus 5%; and in one specific aspect, plus or minus 2%. For example, in one aspect where about is plus or minus 20% of a numeric value, the phrase "from about 10% to about 20%" could include a range from 8% to 24% or 12% to 16%, include any subranges therein.

As used herein, embodiments, aspects, and examples using "comprising" language or other open-ended language can be substituted with "consisting essentially of" and "consisting of" embodiments.

The term "complete and balanced" when referring to a food composition means a food composition that contains all known required nutrients in appropriate amounts and proportions based on recommendations of recognized authorities in the field of animal nutrition, and are therefore capable of serving as a sole source of dietary intake to maintain life or promote production, without the addition of supplemental nutritional sources. Nutritionally balanced pet food and animal food compositions are widely known and widely used in the art, e.g., complete and balanced food compositions formulated according to standards established by the Association of American Feed Control Officials (AAFCO).

All percentages expressed herein are by weight of the composition on a dry matter basis unless specifically stated otherwise. The skilled artisan will appreciate that the term "dry matter basis" means that an ingredient's concentration or percentage in a composition is measured or determined after any free moisture in the composition has been removed.

As used herein, ranges are used herein in shorthand, so as to avoid having to list and describe each and every value within the range. Any appropriate value within the range can be selected, where appropriate, as the upper value, lower value, or the terminus of the range.

All dosages used herein refer to the amount of an ingredient or component or active per body weight of the animal per time period unless the context dictates otherwise. For example. in one embodiment, the histidine or ferulic acid dosage can be expressed as mg/kgBW/day or g/kgBW/day.

As used herein, the singular form of a word includes the plural, and vice versa, unless the context clearly dictates otherwise. Thus, the references "a", "an", and "the" are generally inclusive of the plurals of the respective terms. For example, reference to "a supplement", "a method", or "a food" includes a plurality of such "supplements", "methods", or "foods." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

The methods and compositions and other advances disclosed here are not limited to particular methodology, protocols, and reagents described herein because, as the skilled artisan will appreciate, they may vary. Further, the terminology used herein is for the purpose of describing particular embodiments only, and is not intended to, and does not, limit the scope of that which is disclosed or claimed.

Unless defined otherwise, all technical and scientific terms, terms of art, and acronyms used herein have the meanings commonly understood by one of ordinary skill in the art in the field(s) of the invention, or in the field(s) where the term is used. Although any compositions, methods, articles of manufacture, or other means or materials similar or equivalent to those described herein can be used in the practice of the present invention, certain compositions, methods, articles of manufacture, or other means or materials are described herein.

All patents, patent applications, publications, technical and/or scholarly articles, and other references cited or referred to herein are in their entirety incorporated herein by reference to the extent allowed by law. The discussion of those references is intended merely to summarize the assertions made therein. No admission is made that any such patents, patent applications, publications or references, or any portion thereof, are relevant, material, or prior art. The right to challenge the accuracy and pertinence of any assertion of such patents, patent applications, publications, and other references as relevant, material, or prior art is specifically reserved.

DETAILED DESCRIPTION

The present methods and compositions are based upon the discovery that histidine and ferulic acid provide a synergistic effect for inhibiting glucose production. Specifically, the present methods and compositions utilize histidine and ferulic acid to provide a health benefit to an animal.

In one embodiment, a composition for providing a health benefit to an animal can comprise ferulic acid and histidine, where the composition contains ferulic acid and histidine in therapeutically effective amounts for providing the health benefit to the animal.

In another embodiment, a method for providing a health benefit to an animal can comprise administering a composition to the animal, wherein the composition comprises ferulic acid and histidine in therapeutically effective amounts for providing the health benefit to the animal.

In one embodiment, the health benefit can be selected from the group consisting of prevention of diabetes, treatment of diabetes, delayed onset of diabetes, prevention of pre-diabetes, delayed onset of pre-diabetes, treatment of pre-diabetes, prevention of insulin resistance, treatment of insulin resistance, delayed onset of insulin resistance.

Generally, ferulic acid is present in a therapeutically effective amount, combined with histidine, to provide the health benefit. In one embodiment, ferulic acid can be present in the composition in an amount from about 2 mg to about 2 g. In other aspects, ferulic acid can be present in amounts ranging from about 5 mg to about 1 g, or even about 10 mg to about 500 mg. In another embodiment, ferulic acid can be present in such amounts for supplements.

Generally, histidine is present in a therapeutically effective amount, combined with ferulic acid, to provide the health benefit. In one embodiment, histidine can be present in the composition in an amount from about 0.5 g to about 21 g. In other aspects, histidine can be present in amounts ranging from about 1 g to about 10 g, or even about 1 g to about 5 g. In another embodiment, histidine can be present in a supplement in such amounts or even from about 1 g to about 16 g.

The present composition can be any composition suitable for an animal including food compositions, supplements, treats, pharmaceutical compositions, and the like. In one embodiment, the composition can be a food composition. In one aspect, the composition can be a main meal composition. In another aspect, the composition can be a supplement. In one embodiment, the animal can be a human or companion animal. In one aspect, the animal can be a companion animal. In another aspect, the animal can be a feline. In one aspect, the animal can be a canine. In another aspect, the animal can be a human. As such, the present methods and compositions can be directed and/or formulated for such animals, e.g., formulated for a companion animal or feline.

In one embodiment, the compositions can be food compositions. In one aspect, the composition can further comprise protein, fat, carbohydrates, and fiber. In another embodiment, the composition can further comprise an additive effective for glucose control or diabetic management. Such additives can include any pharmacological treatment (insulin, metformin, etc), or nutritional ingredients for glucose control and diabetes management (glucosidase inhibitor, amylase inhibitor, etc).

Generally, the present food compositions comprise a protein. The protein can be crude protein material and may comprise vegetable proteins such as soybean meal, soy protein concentrate, corn gluten meal, wheat gluten, cottonseed, and peanut meal, or animal proteins such as casein, albumin, and meat protein. Examples of meat protein useful herein include beef, pork, lamb, equine, poultry, fish, and mixtures thereof. In one embodiment, the food compositions can comprises the protein in amounts from about 15%, 20%, 25%, 30%, 35%, 40%, 45%, 50%, 55%, or even 60% to about 25%, 30%, 35%, 40%, 45%, 50%, 55%, 60%, or even 65%, including various subranges within these amounts. In one aspect, the protein can be from about 20% to about 50% of the food composition.

Generally, any type of carbohydrate can be used in the food compositions. Examples of suitable carbohydrates include grains or cereals such as rice, corn, millet, sorghum, alfalfa, barley, soybeans, canola, oats, wheat, rye, triticale and mixtures thereof. The compositions may also optionally comprise other materials such as dried whey and other dairy by-products. In one embodiment, the carbohydrate comprises from about 5% to about 70% of the food composition. In another embodiment, the carbohydrate comprises from about 20% to about 50% of the food compositions. In other aspects, the carbohydrate can be present in amounts from about 5%, 10%, 15%, 20%, 25%, 30%, 35%, or even 40%, to about 20%, 25%, 30%, 35%, 40%, 45%, 50%, 55%, 60, 65%, or 70%.

Generally, the food compositions include fat. Examples of suitable fats include animal fats and vegetable fats. In one aspect, the fat source can be an animal fat source such as tallow or poultry fat. Vegetable oils such as corn oil, sunflower oil, safflower oil, grape seed oil, soy bean oil, olive oil and other oils rich in monounsaturated and polyunsaturated fatty acids, may also be used. In one embodiment, the food compositions can comprises the fat in amounts from about 10%, 15%, 20%, 25%, 30%, or even 35% to about 15%, 20%, 25%, 30%, 35%, 40%, 45%, or even 50%, including various subranges within these amounts. In one aspect, the fat comprises from about 20% to about 40% of the food composition.

The administration can be performed on as-needed basis, an as-desired basis, a regular basis, or intermittent basis. In one aspect, the food composition can be administered to the animal on a regular basis. In one aspect, at least weekly administration can be performed. In another aspect, an administration regimen can comprise at least once daily consumption. Generally, the compositions can be administered to the animal on a basis to achieve at least one of the health benefits disclosed herein. In another embodiment, the composition can be administered on a long-term basis, i.e., for at least 6 months. In other aspects, the long-term basis can be for at least 1 year, 2, years, 3 years, or the life of the animal. The following dosages are based on the amount of the active per body weight of the animal per time period; e.g., mg histidine per kg body weight of the animal per day (mg/kgBW/day). While the composition is generally administered sufficient to achieve a health benefit as described herein, in one embodiment, the administration provides a histidine dosage of about 1 mg/kgBW/day to about 2 g/kgBW/day and/or a ferulic acid dosage of about 0.5 mg/kgBW/day to about 500 mg/kgBW/day. In other aspects, the administration can provide a histidine dosage of about 10 mg/kgBW/day to about 500 mg/kgBW/day, or even about 60 mg/kgBW/day to about 330 mg/kgBW/day. In still other aspects, the administration can provide a ferulic acid dosage of about 0.5 mg/kgBW/day to about 50 mg/kgBW/day, or even about 10 mg/kgBW/day to about 50 mg/kgBW/day.

According to the presently described methods, administration, including administration as part of a dietary regimen, can span a period ranging from parturition through the adult life of the animal. In various embodiments, the animal can be a human or companion animal such as a dog or cat. In certain embodiments, the animal can be a young or growing animal. In other embodiments, administration can begin, for example, on a regular or extended regular basis, when the animal has reached more than about 10%, 20%, 30%, 40%, or 50% of its projected or anticipated lifespan. In some embodiments, the animal can have attained 40, 45, or 50% of its anticipated lifespan. In yet other embodiments, the animal can be older having reached 60, 66, 70, 75, or 80% of its likely lifespan. A determination of lifespan may be based on actuarial tables, calculations, estimates, or the like, and may consider past, present, and future influences or factors that are known to positively or negatively affect lifespan. Consideration of species, gender, size, genetic factors, environmental factors and stressors, present and past health status, past and present nutritional status, stressors, and the like may also influence or be taken into consideration when determining lifespan.

Such administration can be performed for a time required to accomplish one or more objectives described herein, e.g., prevention of diabetes, treatment of diabetes, delayed onset of diabetes, prevention of pre-diabetes, delayed onset of pre-diabetes, treatment of pre-diabetes, prevention of insulin resistance, treatment of insulin resistance, delayed onset of insulin resistance. Other administration amounts may be appropriate and can be determined based on the animal's initial weight as well as other variables such as species, gender, breed, age, desired health benefit, etc.

The moisture content for such food compositions generally varies depending on the nature of the food composition. The food compositions may be dry compositions (e.g., kibble), semi-moist compositions, wet compositions, or any mixture thereof. In one embodiment, the composition can be a pet food composition, and in one aspect, can be a complete and nutritionally balanced pet food. In this embodiment, the pet food may be a "wet food", "dry food", or food of "intermediate moisture" content. "Wet food" describes pet food that is typically sold in cans or foil bags and has a moisture content typically in the range of about 70% to about 90%. "Dry food" describes pet food that is of a similar composition to wet food but contains a limited moisture content typically in the range of about 5% to about 15% or 20% (typically in the form or small biscuit-like kibbles). In one embodiment, the compositions can have moisture content from about 5% to about 20%. Dry food products include a variety of foods of various moisture contents, such that they are relatively shelf-stable and resistant to microbial or fungal deterioration or contamination. Also, in one aspect, dry food compositions can be extruded food products for either humans or companion animals.

The food compositions may also comprise one or more fiber sources. Such fiber sources include fiber that is soluble, insoluble, fermentable, and nonfermentable. Such fibers can be from plant sources such as marine plants but microbial sources of fiber may also be used. A variety of soluble or insoluble fibers may be utilized, as will be known to those of ordinary skill in the art. The fiber source can be beet pulp (from sugar beet), gum arabic, gum talha, psyllium, rice bran, carob bean gum, citrus pulp, pectin, fructooligosaccharide, short chain oligofructose, mannanoligofructose, soy fiber, arabinogalactan, galactooligosaccharide, arabinoxylan, or mixtures thereof.

Alternatively, the fiber source can be a fermentable fiber. Fermentable fiber has previously been described to provide a benefit to the immune system of a companion animal. Fermentable fiber or other compositions known to skilled artisans that provide a prebiotic to enhance the growth of probiotics within the intestine may also be incorporated into the composition to aid in the enhancement of the benefits described herein or to the immune system of an animal.

In some embodiments, the ash content of the food composition ranges from less than 1% to about 15%. In one aspect, the ash content can be from about 5% to about 10%.

Generally, the food composition can be suitable for consumption by an animal, including humans and companion animals such as dogs and cats, as a meal, component of a meal, a snack, or a treat. Such compositions can include complete foods intended to supply the necessary dietary requirements for an animal. Examples of such food compositions include but are not limited to dry foods, wet foods, drinks, bars, frozen prepared foods, shelf prepared foods, and refrigerated prepared foods.

Food compositions may further comprise one or more substances such as vitamins, minerals, antioxidants, probiotics, prebiotics, salts, and functional additives such as palatants, colorants, emulsifiers, and antimicrobial or other preservatives. Minerals that may be useful in such compositions include, for example, calcium, phosphorous, potassium, sodium, iron, chloride, boron, copper, zinc, magnesium, manganese, iodine, selenium, and the like. Examples of additional vitamins useful herein include such fat soluble vitamins as A, D, E, and K. Inulin, amino acids, enzymes, coenzymes, and the like may be useful to include in various embodiments.

In various embodiments, the food compositions contain at least one of (1) one or more probiotics; (2) one or more inactivated probiotics; (3) one or more components of inactivated probiotics that promote health benefits similar to or the same as the probiotics, e.g., proteins, lipids, glycoproteins, and the like; (4) one or more prebiotics; and (5) combinations thereof. The probiotics or their components can be integrated into the food compositions (e.g., uniformly or non-uniformly distributed in the compositions) or applied to the food compositions (e.g., topically applied with or without a carrier). Such methods are known to skilled artisans, e.g., U.S. Pat. No. 5,968,569 and related patents.

Typical probiotics include, but are not limited to, probiotic strains selected from Lactobacilli, Bifidobacteria, or Enterococci, e.g., *Lactobacillus reuteii, Lactobacillus acidophilus, Lactobacillus animalis, Lactobacillus ruminis, Lactobacillus johnsonii, Lactobacillus casei, Lactobacillus paracasei, Lactobacillus rhamnosus, Lactobacillus fermentum,* and *Bifidobacterium* sp., *Enterococcus faecium* and *Enterococcus* sp.

Generally, the food compositions can contain probiotics in amounts sufficient to supply from about $10^4$ to about $10^{12}$ cfu/animal/day, in one aspect, from $10^5$ to about $10^{11}$ cfu/animal/day, and in one specific aspect, from $10^7$ to $10^{10}$ cfu/animal/day. When the probiotics are killed or inactivated, the amount of killed or inactivated probiotics or their components should produce a similar beneficial effect as the live microorganisms. Many such probiotics and their benefits are known to skilled artisans, e.g., EP1213970B1, EP1143806B1, U.S. Pat. No. 7,189,390, EP1482811B1, EP1296565B1, and U.S. Pat. No. 6,929,793. In another embodiment, the probiotics can be encapsulated in a carrier using methods and materials known to skilled artisans.

As stated, the food compositions may contain one or more prebiotics, e.g., fructo-oligosaccharides, gluco-oligosaccharides, galacto-oligosaccharides, isomalto-oligosaccharides, xylo-oligosaccharides, soybean oligosaccharides, lactosucrose, lactulose, and isomaltulose. In one embodiment, the prebiotic can be chicory root, chicory root extract, inulin, or combinations thereof. Generally, prebiotics can be administered in amounts sufficient to positively stimulate the healthy microflora in the gut and cause these "good" bacteria to reproduce. Typical amounts range from about one to about 10 grams per serving or from about 5% to about 40% of the recommended daily dietary fiber for an animal. The probiotics and prebiotics can be made part of the composition by any suitable means. Generally, the agents can be mixed with the composition or applied to the surface of the composition, e.g., by sprinkling or spraying. When the agents are part of a kit, the agents can be admixed with other materials or in their own package. Typically, the food composition contains from about 0.1 to about 10% prebiotic, in one aspect, from about 0.3 to about 7%, and in one specific aspect, from about 0.5 to 5%, on a dry matter basis. The prebiotics can be integrated into the compositions using methods known to skilled artisans, e.g., U.S. Pat. No. 5,952,033.

Sources of ferulic acid that can be used include sugar-beet pulp, popcorn, bamboo shoots, whole grain rye, whole grain oat, corn, red beet, eggplant, water dropwort, brown long grain rice, burdock, coffee, pasta, soybean, and grapefruit.

A skilled artisan can determine the appropriate amount of food ingredients, vitamins, minerals, probiotics, prebiotics, antioxidants, or other ingredients to be used to make a particular composition to be administered to a particular animal. Such artisan can consider the animal's species, age, size, weight, health, and the like in determining how best to formulate a particular composition comprising such ingredients. Other factors that may be considered include the desired dosage of each component, the average consumption of specific types of compositions by different animals (e.g., based on species, body weight, activity/energy demands, and the like), and the manufacturing requirements for the composition.

In a further aspect, the present disclosure provides kits suitable for administering food compositions to animals. The kits comprise in separate containers in a single package or in separate containers in a virtual package, as appropriate for the kit component, one or more of (1) one or more ingredients suitable for consumption by an animal; (2) instructions for how to combine the ingredients and other kit components to produce a composition useful for providing a health benefit as described herein; (3) instructions for how to use the food composition to obtain such benefits; (4) one or more probiotics; (5) one or more inactivated probiotics; (6) one or more components of inactivated probiotics that promote health benefits similar to or the same as the probiotics, e.g., proteins, lipids, glycoproteins, and the like; (7) one or more prebiotics; (8) a device for preparing or combining the kit components to produce a composition suitable for administration to an animal; and (9) a device for administering the combined or prepared kit components to an animal. In one embodiment, the kit comprises one or more ingredients suitable for consumption by an animal. In another embodiment, the kit comprises instructions for how to combine the ingredients to produce a composition useful for obtaining a health benefit as described herein.

When the kit comprises a virtual package, the kit is limited to instructions in a virtual environment in combination with one or more physical kit components. The kit contains components in amounts sufficient for to obtain a health benefit as described herein. Typically, the kit components can be admixed just prior to consumption by an animal. The kits may contain the kit components in any of various combinations and/or mixtures. In one embodiment, the kit contains a container of food for consumption by an animal. The kit may contain additional items such as a device for mixing ingredients or a device for containing the admixture, e.g., a food bowl. In another embodiment, the food compositions can be mixed with additional nutritional supplements such as vitamins and minerals that promote good health in an animal. The components can be each provided in separate containers in a single package or in mixtures of various components in different packages. In some embodiments, the kits comprise one or more other ingredients suitable for consumption by an animal. In one aspect, such kits can comprise instructions describing how to combine the ingredients to form a food composition for consumption by the animal, generally by mixing the ingredients or by applying optional additives to the other ingredients, e.g., by sprinkling nutritional supplements on a food composition.

In a further aspect, a means for communicating information about or instructions for one or more of (1) using a food composition for obtaining one of the health benefits described herein; (2) contact information for consumers to use if they have a question regarding the methods and compositions described herein; and (3) nutritional information about the food composition can be provided. The communication means can be useful for instructing on the benefits of using the present methods or compositions and communicating the approved methods for administering food compositions to an animal. The means comprises one or more of a physical or electronic document, digital storage media, optical storage media, audio presentation, audiovisual display, or visual display containing the information or instructions. In one aspect, the means can be selected from the group consisting of a displayed website, a visual display kiosk, a brochure, a product label, a package insert, an advertisement, a handout, a public announcement, an audiotape, a videotape, a DVD, a CD-ROM, a computer readable chip, a computer readable card, a computer readable disk, a USB device, a FireWire device, a computer memory, and any combination thereof.

In another aspect, methods for manufacturing a food composition comprising one or more other ingredients suitable for consumption by an animal, e.g., one or more of protein, fat, carbohydrate, fiber, vitamins, minerals, probiotics, prebiotics, and the like, can comprise admixing one or more of the ingredients suitable for consumption by an animal. The composition can be made according to any method suitable in the art.

In another aspect, a package useful for containing compositions described herein can comprise at least one material suitable for containing the food composition and a label affixed to the package containing a word or words, picture, design, acronym, slogan, phrase, or other device, or combination thereof that indicates that the contents of the package contains the food composition. In some embodiments, the label affixed to the package contains a word or words, picture, design, acronym, slogan, phrase, or other device, or combination thereof that indicates that the contents of the package contains the food composition with beneficial properties relating to a health benefit described herein. In one aspect, such device can comprise the words "for diabetes," treats diabetes," "delays onset of diabetes" or an equivalent or similar expression printed on the package. Any package configuration and packaging material suitable for containing the composition can be used herein, e.g., bag, box, bottle, can, pouch, and the like manufactured from paper, plastic, foil, metal, and the like. In one embodiment, the package contains a food composition adapted for a particular animal such as a human, canine, or feline, as appropriate for the label, in one aspect, a companion animal food composition for dogs or cats. In one embodiment, the package can be a can or pouch comprising a food composition described herein. In various embodiments, the package further comprises at least one window that permit the package contents to be viewed without opening the package. In some embodiments, the window can be a transparent portion of the packaging material. In others, the window can be a missing portion of the packaging material.

EXAMPLES

The invention can be further illustrated by the following example, although it will be understood that this example is included merely for purposes of illustration and is not intended to limit the scope of the invention unless otherwise specifically indicated.

Example 1—In Vitro Study

A cellular bioassay was established according to a method described by Okamoto et al. (Establishment and characterization of a novel method for evaluating gluconeogenesis using hepatic cell lines, H4IIE and HepG2, *Archives of Biochemistry and Biophysics*, Volume 491, Issues 1-2, November 2009, Pages 46-52; Takashi Okamoto, Naohide Kanemoto, Takashi Ban, Toshiki Sudo, Keisuke Nagano, Ichiro Niki.) (FIG. 1). Briefly, H4IIE cells pre-cultured at high density were seeded into a 12-well plate at a density of $5.714 \times 10^5$ cells/cm$^2$ and cultured for 24 h in EMEM supplemented with 10% FCS. Thereafter, cells were washed twice with PBS, followed by pre-incubation in phenol red-glucose-pyruvate-free DMEM supplemented with 1 g/L glucose for another 16 h. The assay was started by switching the medium for KHH Buffer in the presence of gluconeogenesis-inducing substrates (1 mM sodium pyruvate and 10 mM lactate). Compounds were added at different concentrations and tested in duplicate. 10 mM of metformin was included as a positive control for inhibition of gluconeogenesis. The conditioned medium was collected after 6 h of incubation (stored at −80° C.). The cells remaining in the wells are washed once with PBS and then stored dry at −20° C.). The medium is used to assay glucose content using a fluorometric glucose assay kit. Frozen cells' proteins are first extracted and then quantified, to normalize the glucose results. Components were tested in at least two independent experiments performed at different cell passages.

The selected compounds (Histidine and Ferulic acid) were tested individually to assess their inhibitory effect on hepatic glucose production (Table 1) using a range of concentrations determined from previous internal knowledge and literature. Additional experiments on individual compounds were conducted: the amino acid arginine and leucine to test the specificity of histidine effects against other amino acids. In addition, interactions and synergies between compounds were further explored using combined formulations, for which detailed information is provided in Table 1.

TABLE 1

| Conditions | Dose/Ingredients | Histidine (mM) | Arginine (mM) | Leucine (mM) | Ferulic Acid (μM) |
|---|---|---|---|---|---|
| Controls | Basal | — | — | — | — |
|  | SLP | — | — | — | — |
|  | Metformin | — | — | — | — |
| Single Compounds | His 0.2 mM | 0.2 | — | — | — |
|  | His 0.5 mM | 0.5 | — | — | — |
|  | His 1 mM | 1.0 | — | — | — |
|  | His 2 mM | 2.0 | — | — | — |
|  | His 20 mM | 20.0 | — | — | — |
|  | Arg 0.2 mM | — | 0.2 | — | — |
|  | Arg 2 mM | — | 2.0 | — | — |
|  | Arg 20 mM | — | 20.0 | — | — |
|  | Leu 0.2 mM | — | — | 0.2 | — |
|  | Leu 2 mM | — | — | 2.0 | — |
|  | Leu 20 mM | — | — | 20.0 | — |
|  | FA 0.5 μM | — | — | — | 0.5 |
|  | FA 0.8 μM | — | — | — | 0.8 |
|  | FA 1 μM | — | — | — | 1.0 |
|  | FA 2 μM | — | — | — | 2.0 |
|  | FA 4 μM | — | — | — | 4.0 |
| Two Compounds | His 1 mM + FA 1 μM | 1.0 | — | — | 1.0 |
|  | His 1 mM + FA 2 μM | 1.0 | — | — | 2.0 |
|  | His 2 mM + FA 2 μM | 2.0 | — | — | 2.0 |
|  | His 0.2 mM + FA 0.5 μM | 0.2 | — | — | 0.5 |
|  | His 0.2 mM + FA 0.8 μM | 0.2 | — | — | 0.8 |
|  | His 0.5 mM + FA 0.5 μM | 0.5 | — | — | 0.5 |
|  | His 0.5 mM + FA 0.8 μM | 0.5 | — | — | 0.8 |

For data analysis described herein, results are expressed as relative glucose produced in every treatment compared to the glucose produced using SLP treatment. Each condition was repeated in duplicates by each experiment and duplicates by each measurement, resulting in 4 values per experiment. Independent experiments were performed, using different cells passages in each condition. In selected cases, synergistic effects were further evaluated using an adapted approach from Quantitative Methods for Assessing Drug Synergism, where assessment of additive, synergistic or antagonist effect can be described using isobolograms ((Tallarida, R. J. (2011) Quantitative methods for assessing drug synergism. Genes Cancer 2, 1003-1008. doi: 10.1177/1947601912440575; Tallarida, R. J. (2012) Revisiting the isobole and related quantitative methods for assessing drug synergism. J Pharmacol Exp Ther 342, 2-8. doi: 10.1124/jpet.112.193474)). Sodium Pyruvate (1 mM) and Sodium Lactate (10 mM) was used to induce gluconeogenesis in H4IIE cells. Sodium Pyruvate and Lactate (SLP) treatment induced significant hepatic glucose production compared to Basal treatment and is considered as the reference group for our assay. A low glucose production of 8.18%±4.2 was observed under the basal condition. The SLP condition induced a high glucose production and is used as the 100% glucose production reference for all the results.

Metformin is a well-known negative regulator of hepatic glucose production. A dose of 10 mM metformin was employed in our cell culture experiments as a positive control. A strong inhibitory effect on hepatic glucose production was induced, as noted with low glucose production: 9.71%±4.2. Considering that the control provides the expected results and has a low variability, the model was validated and was further used with treatments including the compounds of interest.

Under these experimental conditions, histidine doses at 0.2 mM and 0.5 mM did not significantly inhibit the glucose production compared to the SLP condition (93.70%±10.85 and 87.00%±17.20% glucose production). Higher doses of histidine (e.g. 1 mM, 2 mM and 20 mM) inhibited glucose production down to 52.67%±4.16, 39.19%±7.44, 8.39%±2.49, respectively. Effects from incremental increase in histidine doses were also significant, thus describing a significant dose response on the inhibition of gluconeogenesis in H4IIE cell system.

In order to test the specificity of histidine against other amino acids, two amino acids were selected, one glucogenic and one non-glucogenic, to test their effects. The doses for these amino acids were adapted from the histidine experiment, using 0.2 mM, 2 mM and 20 mM concentrations. Arginine exhibited a statistically significant dose-dependent response in inhibiting the glucose production compared to the SLP condition (0.2 mM: 81.44%±2.72, 2 mM: 65.01%±11.52% and 20 mM: 45.40%±3.57 glucose production). Yet, the effect size was weaker compared to histidine for the same concentrations. Leucine showed a mild inhibition of glucose production, without clear dose response, compared to the SLP condition (0.2 mM: 84.69%±1.05, 2 mM: 75.37%±0.36 and 20 mM: 83.76%±7.30 glucose production). Since histidine has a stronger dose response effect (93.7%±10.85, 39.19%±7.44 and 8.39%±2.49) towards the inhibition of glucose production than arginine, and leucine has minimal effects, the experiment further strengthens the specificity of the effects observed in this in vitro model.

Ferulic acid significantly inhibited glucose production to 85.67%±3.81, 81.51%±11.70, 61.38%±15.82, 36.57%±6.02 and 25.08%±5.03 glucose production at 0.5 μM, 0.8 μM, 1 μM, 2 μM, and 4 μM respectively, which was significantly lower than the SLP condition, independently of the dose. As such, ferulic acid demonstrated a strong dose-dependent inhibition of gluconeogenesis in H4IIE cell system.

As individual compounds, the following was observed. For histidine, 0.5 mM, 1 mM, and 2 mM histidine inhibited gluconeogenesis down to 87.00%±17.2, 52.67%±4.16 and 39.19%±7.44, respectively. Doubling the histidine dose from 0.5 mM to 1 mM led to a 52% inhibiting effect, 1 mM to 2 mM led to a 25% inhibiting effect. For ferulic acid, 1 μM and 2 μM ferulic acid inhibited gluconeogenesis down to 61.38%±15.82 and, 36.57%±6.02, respectively. Doubling the ferulic acid dose from 0.5 μM to 1 μM led to a 30% inhibition, doubling from 1 μM to 2 μM led to a 40% inhibiting effect and doubling it again from 2 μM to 4 μM led to a 32% inhibition. Optimal dose response appears to be within the 1-2 μM.

For combinations, 1 mM histidine+1 μM ferulic acid reduced the glucose production down to 27.69%±3.54. The reduction in glucose was significantly lower than the SLP control, was significantly lower than the compounds used individually at the same doses, and was generally lower than the effect obtained when doubling the dose of individual compounds. 1 mM histidine+2μ4 ferulic acid reduced the glucose production down to 23.67%±11.03. The effect was significantly lower than the SLP control, was significantly lower than the effect obtained when doubling the dose of histidine, and was generally lower than the effect obtained with 2 μM ferulic acid alone. 2 mM histidine+2μ4 ferulic acid significantly reduced glucose production down to 13.05%±8.75. The effect was significantly lower than the SLP control, and was significantly lower than the effects obtained than individual compounds at the same dose. Notably, the effect size observed when the two compounds were combined was greater than using the compounds individually, or when doubling the individual compounds dose. Such a finding indicates potential synergy.

Figure 2:
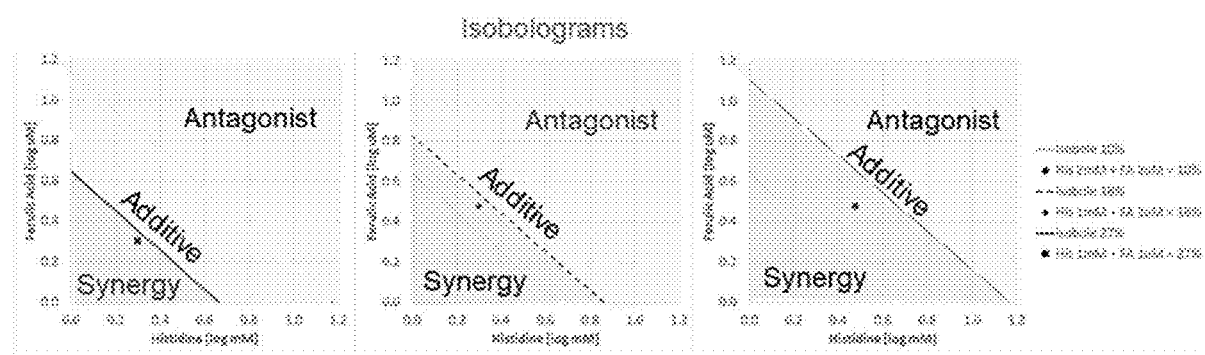
FIG. 2 is an isobologram of three isoboles showing synergistic effects of histidine and ferulic acid, corresponding to the mixtures that are predicted to reach 3 responses (respectively 10%, 18% and 27% glucose production).

Dose responses (glucose production relative to REF=SLP=100%) could be modelled as linear for both histidine (A) and ferulic acid (B) when both dose and response are expressed on log scales. Under the assumption that this linearity was maintained for mixtures of histidine and ferulic acid, it is possible to predict all mixtures that would reach a certain response. These mixtures predicted to achieve equal response can be visualized as a line on a figure representing all possible mixtures, and termed isobole (FIG. 2). A figure representing many such isoboles is called an isobologram.

FIG. 2 shows three isoboles corresponding to the mixtures that are predicted to reach three responses (respectively 10%, 18% and 27% glucose production). These three isoboles are represented because the three responses correspond to the responses obtained for the three tested mixtures of histidine and ferulic acid. Briefly, an isobole represents a line along which mixes of bioactives shall remain if they have only additive effects. The intersection of the isobole with the axis corresponds to the dose of the individual compounds to induce the same effect as the combination of compounds along the isobole line. If the experimental data are not falling on the isobole, the model indicates either antagonist effect if the value is higher than the isobole, or a synergistic effect is the value is lower than the isobole.

The fact that all three tested mixtures are below their corresponding isoboles shows that there is a synergistic effect (i.e. the doses of histidine and ferulic acid required to achieve a given response are lower than expected by the purely additive model represented by the isobole).

When reviewing effects of lower doses (0.2 mM histidine+0.5 μM ferulic acid, 0.2 mM histidine+0.8 μM ferulic acid, 0.5 mM histidine+0.5 μM ferulic acid), the effect size observed when the two compounds were combined may be lower than when using the compounds individually, but did not appear to be lower than twice the doses of individual compounds. Application of an isobole approach did not reveal synergies between compounds when using lower doses.

In the specification, there have been disclosed certain embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A composition for providing at least one health benefit to an animal, the composition comprising ferulic acid and histidine, wherein the composition contains the ferulic acid and the histidine in therapeutically effective amounts for providing the at least one health benefit to the animal,
    wherein the ferulic acid is present in the composition in an amount from about 2 mg to about 2 g, and the histidine is present in the composition in an amount from about 0.5 g to about 21 g,
    wherein the at least one health benefit is selected from the group consisting of prevention of diabetes, treatment of diabetes, delayed onset of diabetes, prevention of pre-diabetes, delayed onset of pre-diabetes, treatment of pre-diabetes, prevention of insulin resistance, treatment of insulin resistance, and delayed onset of insulin resistance.

2. The composition of claim 1, wherein the ferulic acid is present in the composition in an amount from about 5 mg to about 1 g, and the histidine is present in the composition in an amount from about 1 g to about 10 g.

3. The composition of claim 1, wherein the ferulic acid is present in the composition in an amount from about 10 mg to about 500 mg.

4. The composition of claim 1, wherein the histidine is present in the composition in an amount from about 1 g to about 5 g.

5. The composition of claim 1, wherein the composition is a main meal composition.

6. The composition of claim 1, wherein the composition is a supplement.

7. The composition of claim 1, wherein the composition is formulated for a companion animal.

8. The composition of claim 1, wherein the composition is formulated for a feline.

9. The composition of claim 1, wherein the composition further comprises protein, fat, carbohydrates, and fiber.

10. The composition of claim 1, wherein the composition further comprises an additive effective for glucose control or diabetic management.

11. A method for providing at least one health benefit to an animal, the method comprising administering a composition to the animal, wherein the composition comprises ferulic acid and histidine in therapeutically effective amounts to provide the at least one health benefit to the animal,
    wherein the ferulic acid is present in the composition in an amount from about 2 mg to about 2 g, and the histidine is present in the composition in an amount from about 0.5 g to about 21 g,
    wherein the at least one health benefit is selected from the group consisting of prevention of diabetes, treatment of diabetes, delayed onset of diabetes, prevention of pre-diabetes, delayed onset of pre-diabetes, treatment of pre-diabetes, prevention of insulin resistance, treatment of insulin resistance, and delayed onset of insulin resistance.

12. The method of claim 11, wherein the composition is administered to the animal on a regular basis.

13. The method of claim 11, wherein the administration provides a histidine dosage of about 1 mg/kgBW/day to about 2 g/kgBW/day and a ferulic acid dosage of about 0.5 mg/kgBW/day to about 500 mg/kgBW/day.

14. The method of claim 11, wherein the ferulic acid is present in the composition in an amount from about 5 mg to about 1 g, and the histidine is present in the composition in an amount from about 1 g to about 10 g.

15. The method of claim 11, wherein the ferulic acid is present in the composition in an amount from about 10 mg to about 500 mg and the histidine is present in the composition in an amount from about 1 g to about 5 g.

16. The method of claim 11, wherein the composition is a main meal composition.

17. The method of claim 11, wherein the composition is a supplement.

18. The method of claim 11, wherein the composition is a formulated for a companion animal.

19. The method of claim 11, wherein the composition is formulated for a feline.

20. The method of claim 11, wherein the composition further comprises an additive effective for glucose control or diabetic management.

\* \* \* \* \*